United States Patent
Fleischer et al.

(10) Patent No.: US 11,242,603 B2
(45) Date of Patent: Feb. 8, 2022

(54) PULSED ELECTROLYSIS WITH REFERENCE TO THE OPEN CIRCUIT VOLTAGE

(71) Applicant: Siemens Aktiengesellschaft, Munich (DE)

(72) Inventors: Maximilian Fleischer, Höhenkirchen (DE); Kerstin Wiesner-Fleischer, Höhenkirchen (DE); Andreas Engelbrecht, Hummeltal (DE); Martin Hämmerle, Bayreuth (DE); Ralf Moos, Bayreuth (DE)

(73) Assignee: SIEMENS ENERGY GLOBAL GMBH & CO. KG, Munich (DE)

( * ) Notice: Subject to any disclaimer, the term of this patent is extended or adjusted under 35 U.S.C. 154(b) by 218 days.

(21) Appl. No.: 16/484,314

(22) PCT Filed: Feb. 1, 2018

(86) PCT No.: PCT/EP2018/052548
§ 371 (c)(1),
(2) Date: Aug. 7, 2019

(87) PCT Pub. No.: WO2018/145996
PCT Pub. Date: Aug. 16, 2018

(65) Prior Publication Data
US 2019/0382906 A1    Dec. 19, 2019

(30) Foreign Application Priority Data
Feb. 8, 2017   (DE) .................. 10 2017 201 988.3

(51) Int. Cl.
*C25B 3/25* (2021.01)
*C25B 15/02* (2021.01)
(Continued)

(52) U.S. Cl.
CPC .............. *C25B 3/25* (2021.01); *C25B 9/65* (2021.01); *C25B 15/02* (2013.01); *C07C 9/04* (2013.01);
(Continued)

(58) Field of Classification Search
CPC .. C25B 3/32; C25B 3/26; C25B 15/02; C25B 15/03
See application file for complete search history.

(56) References Cited

U.S. PATENT DOCUMENTS

| | | | |
|---|---|---|---|
| 2005/0185447 A1 | 8/2005 | Kuhr et al. | 365/151 |
| 2013/0186771 A1 | 7/2013 | Zbai et al. | 205/440 |
| 2015/0096897 A1* | 4/2015 | Hashiba | C25B 9/19 205/450 |

FOREIGN PATENT DOCUMENTS

| | | | | |
|---|---|---|---|---|
| AU | 2018/217852 A1 | 8/2019 | ............. | C25B 15/02 |
| CN | 1896896 A | 1/2007 | ........... | G05B 19/406 |

(Continued)

OTHER PUBLICATIONS

Lee et al. ("Electrocatalytic activity of Cu electrode in electroreduction of CO2", Electrochimica Acta, vol. 46, Issue 19, Jun. 15, 2001, pp. 3015-3022). (Year: 2001).*

(Continued)

*Primary Examiner* — Alexander W Keeling
(74) *Attorney, Agent, or Firm* — Slayden Grubert Beard PLLC

(57) ABSTRACT

Various embodiments include an electrolysis method comprising: applying a pulsed voltage or a pulsed current between an anode and a cathode; repeatedly measuring a respective current OCP at the cathode in a zero-current state relative to a reference system; and controlling the pulsed voltage or the pulsed current so a working potential of the cathode in the current-carrying state with respect to the reference system has a defined progression relative to the (Continued)

respective current OCP. The defined progression includes a first phase at a cathodic level and a second phase at an anodic level.

21 Claims, 4 Drawing Sheets

(51) Int. Cl.
    *C25B 9/65* (2021.01)
    *C07C 9/04* (2006.01)
    *C07C 9/06* (2006.01)
    *C07C 9/08* (2006.01)
    *C07C 31/02* (2006.01)
    *C07C 47/02* (2006.01)
    *C07C 53/00* (2006.01)

(52) U.S. Cl.
    CPC .............. *C07C 9/06* (2013.01); *C07C 9/08* (2013.01); *C07C 31/02* (2013.01); *C07C 47/02* (2013.01); *C07C 53/00* (2013.01)

(56) References Cited

FOREIGN PATENT DOCUMENTS

| | | | | |
|---|---|---|---|---|
| CN | 103119017 A | 5/2013 | ............ | C07C 51/15 |
| CN | 204625801 U | 9/2015 | ............ | C25B 9/00 |
| DE | 10 2013 105 605 A1 | 12/2013 | ............ | C25B 3/04 |
| JP | 08296077 A | 11/1996 | ............ | B01D 53/32 |
| WO | 02/077633 A1 | 10/2002 | ............ | G01N 27/416 |
| WO | 2018/145996 A1 | 8/2018 | ............ | C25B 15/02 |

OTHER PUBLICATIONS

Taylor ("Adventures in Pulse/Pulse Reverse Electrolytic Processes: Explorations and Applications in Surface Finishing", Journal of Applied Surface Finishing, vol. 3, 4, 2008, pp. 178-189). (Year: 2008).*

Chinese Office Action, Application No. 201880010741.4, 9 pages, dated Nov. 26, 2020.

Shiratsuchi et al., "Pulsed Electroreduction of Co2 on Copper Electrodes," The Electrochemical Society, Inc., Journal of The Electrochemical Society, vol. 140, No. 12, pp. 3479-3482, Dec. 1993.

Nogami et al., "Pulsed Electroreduction of CO2 on Copper Electrodes—II" The Electrochemical Society, Inc., Journal of the Electrochemical Society, vol. 141, No. 5, pp. 1138-1142, May 1994.

Jermann et al., "Long-term activation of the copper cathode in the course of CO2 reduction," Elsevier Science Ltd., Electrochimica Acta, vol. 39, Issue 11-12, pp. 1891-1896, Aug. 1994.

Warner et al., "A fundamental study of a novel dynamic electrochemical technique for the measurement of trace amounts of arsenic and antimony in molten zinc," Elsevier Science Ltd., Solid State Ionics, vol. 136-137, pp. 589-601, Nov. 2, 2000.

Lee et al., "Electrocatalytic activity of Cu electrode in electroreduction of CO2," Elsevier Science Ltd., Electrochimica Acta, vol. 46, Issue 19, pp. 3015-3022, Jun. 15, 2001.

German Office Action, Application No. 10 2017 201 988.3, 10 pages, dated Oct. 2, 2017.

International Search Report and Written Opinion, Application No. PCT/EP2018/052548, 21 pages, dated May 29, 2018.

* cited by examiner

PULSED ELECTROLYSIS WITH REFERENCE TO THE OPEN CIRCUIT VOLTAGE

CROSS-REFERENCE TO RELATED APPLICATIONS

This application is a U.S. National Stage Application of International Application No. PCT/EP2018/052548 filed Feb. 1, 2018, which designates the United States of America, and claims priority to DE Application No. 10 2017 201 988.3 filed Feb. 8, 2017, the contents of which are hereby incorporated by reference in their entirety.

TECHNICAL FIELD

The present disclosure relates to electrolysis. Various embodiments may include electrolysis methods in which a pulsed voltage is applied between an anode and a cathode, and/or electrolysis apparatus having an anode, a cathode, a reference system, and a voltage source for applying a pulsed voltage between the anode and the cathode.

BACKGROUND

In an electrolysis apparatus having a suitable electrolyte, it is possible by a customary method to convert $CO_2$ or CO as reactant with the aid of a typically copper-containing catalyst in a one-stage process to higher-value products such as $CH_4$, $C_2H_4$, $C_2H_6$ or else alcohols, aldehydes or acids. As is also customary in the case of water electrolysis, the aim is a steady-state operating point, i.e. a constant current density, or else a constant potential on the working electrode. Over copper-containing catalysts, however, inadequate long-term stability of the catalyst and a decrease in the selectivity for carbon-containing reduction products, for example $CH_4$, $C_2H_4$, is always observed. There is always a corresponding increase here in the competing reaction of hydrogen evolution (HER). This phenomenon has to date been attributed to morphological changes in the catalyst surface and the associated loss of active crystal orientations and to poisoning phenomena, for example deactivation by deposition of insoluble reduction products on the catalyst surface, such as carbon or other impurities formed from reagents used (Shiratsuchi et al., J. Electrochem. Soc., Vol. 140, No. 12, 1993; Hermann et al., Electrochimica Acta, Vol. 39, 35 No. 11/12, pages 1891 to 1896, 1994).

In the literature published to date, there are only a few studies that address the problem of long-term stability. In 1993, Shiratsuchi et al. (see above) conducted electrolysis with pulsed potential (cathodic and anodic components) and showed that, with different ratios of anodic to cathodic pulse duration—the result is a voltage profile in the form of a square wave, a rise in Faraday efficiency (FE) for $CH_4$ and $C_2H_4$ of up to 20% is possible. In the case of an electrolysis duration of about 25 hours, the Faraday efficiency for methane in pulsed operation rises to just over 10%, whereas, in the case of constant potential, it has already fallen to below 1% after about 6 hours. The efficiency for ethene rises to about 25% but appears to fall again from nearly 17 hours. What is also remarkable is the observed suppression of $H_2$ formation (about 20% FE pulsed relative to about 80% FE in constant operation).

Lee et al. (Lee et al., Electrochimica Acta, 46, pages 3015-3022, 2001) likewise worked with rectangular pulsed operation and showed an increase in electrode mass in constant operation and a decrease in electrode mass in pulsed operation. From this, they concluded the dissolution of copper ions and formation of $Cu_2O$ via copper hydroxide as intermediate. However, the Faraday efficiencies for $CH_4$ are only 20% at most; that for $C_2H_4$ is less than 5%. A broader parameter study was conducted in 1994 by Nogami et al. (Nogami et al., J. Electrochem. Soc., Vol. 141, No. 5, 1994). Under particular conditions, this achieved Faraday efficiencies for methane of 50% over an electrolysis duration of 10 hours. However, the efficiency for ethene does not quite reach 10%.

A further approach was tried by Jermann et al. (see above). In this case, three voltage pulses in sawtooth form at a very high anodic potential were inserted every 5 minutes to 1.1 V versus Ag/AgCl, with the focus on the reactivation of the electrode by removal of deactivating species on the surface. However, it was not possible by this pulsed method to reproduce the retention of the FE shown for $CH_4$ of >40% over more than 45 hours.

In conclusion, potential pulses have already been described for improving for long-term stability of the catalyst and controlling product selectivity. However, the pulsed operation requires not only the energy for the generation of the products but also energy for the regeneration/activation of the catalyst. The latter is a loss that can make economic utilization unviable. The article "Electrocatalytic activity of Cu electrode in electroreduction of $CO_2$" by J. Lee, Y. Tak, Electrochim, Acta 2001, 46, 3015-3022, discloses pulsed electroreduction. At an OCP of −0.05 V, a cathodic potential of −2.1 V is applied to a copper electrode for 10 s and then an anodic potential of 0.0 V for 5 s. Document DE 10 2013 105 605 A1 discloses a method of electrolytic synthesis of methanol and methane. For a higher efficiency, a pulsed current supply is used. Operation with reversed polarity of power supply is possible on a regular basis or as required.

SUMMARY

The teachings of the present disclosure describe electrolysis methods and/or apparatus by which Faraday efficiency can be kept high over a longer period. For example, some embodiments include aN electrolysis method comprising the steps of: applying a pulsed voltage or establishing a pulsed current between an anode and a cathode, characterized by repeated measurement of a respective current OCP that the cathode possesses in a zero-current state relative to a reference system, and controlling the pulsed voltage or the pulsed current between the anode and the cathode such that a working potential of the cathode in the current-carrying state with respect to the reference system has a defined progression (PF) relative to the respective current OCP, where the defined progression (PF) has at least one phase ($t_k$) at a cathodic level and at least one phase ($t_a$) at an anodic level.

In some embodiments, there is a galvanostatic operating regime having a defined current progression with a sequence of phases with anodic and cathodic current level is chosen, where the defined current progression is readjusted dynamically with the measured OCP.

In some embodiments, a hydrocarbon is obtained in a one-stage process from carbon monoxide or carbon dioxide.

In some embodiments, a catalyst, especially a copper-containing catalyst, is used.

In some embodiments, an aqueous electrolyte is used.

In some embodiments, the OCP changes during the electrolysis method.

In some embodiments, the reference system used is a silver/silver chloride system.

In some embodiments, the working potential of the cathode in the current-carrying state and the OCP are negative and, at the same time, the working potential of the cathode is temporarily at an anodic level.

In some embodiments, the working potential of the cathode at the anodic level is below an initial OCP measurable at the start of the electrolysis method.

In some embodiments, there is regular repetition of a duration of the phase ($t_a$) at the anodic level below 10 s and a duration of the phase ($t_k$) at the cathodic level above 10 s.

In some embodiments, the duration of the phase ($t_a$) at the anodic level is within a range from 2 s to 7 s, especially 5 s, and the duration of the phase ($t_k$) at the cathodic level is within a range from 20 s to 100 s, especially within a range from 25 s to 50 s.

In some embodiments, the pulsed voltage or the pulsed current has a square wave profile, a stepped profile or a multilevel profile.

In some embodiments, any energy which is released on reversal of polarity of the cathode is stored in an intermediate storage means.

As another example, some embodiments include an electrolysis apparatus having an anode, a cathode, a reference system and a voltage source for applying a pulsed voltage or a current source for establishing a pulsed current between the anode and the cathode, characterized by a measurement unit for repeated measurement of a respective current OCP that the cathode possesses in a zero-current state with respect to the reference system, and a control unit for controlling the pulsed voltage or the pulsed current between the anode and the cathode in such a way that a working potential of the cathode in the current-carrying state with respect to the reference system has a defined progression (PF) relative to the respective current OCP, wherein the defined progression (PF) has at least one phase ($t_k$) at a cathodic level and at least one phase ($t_a$) at an anodic level.

BRIEF DESCRIPTION OF THE DRAWINGS

The present teachings are elucidated in detail by the appended drawings, which show.

DETAILED DESCRIPTION

Figure 1:
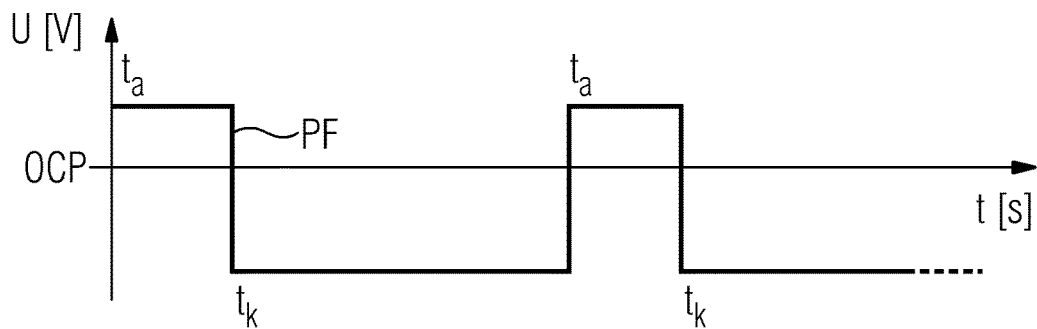
FIG. 1 a schematic diagram of pulsed operation with reference to the OCP potential.

Some embodiments of the teachings of the present disclosure include electrolysis methods, in which a pulsed voltage is applied between an anode and a cathode or a pulsed current is established. The electrolysis cell is thus operated not with a DC voltage but with a specific AC voltage, namely a pulsed voltage, or with a specific alternating current, namely a pulsed current. For this purpose, some embodiments use a potentiostat or a galvanostat. A pulsed voltage includes not just a square-wave voltage profile but also profiles that have flanks with stepwise or continuous alteration of the potential for the transitions between cathodic and anodic potential or vice versa. The same applies to pulsed current.

In some embodiments, there is repeated measurement of a respective current OCP (open circuit potential) that the cathode possesses in a zero-current state relative to a reference system, or alternatively definition of an OCP progression. There is thus dynamic or continual determination of the current OCP, in each case as instantaneous individual value, with electrical separation of the anode and the cathode from one another.

In some embodiments, there is then control of the pulsed voltage or of the pulsed current between the anode and the cathode in such a way that a working potential of the cathode in the current-carrying state, with respect to the reference system, has a defined progression relative to the respective current OCP. Thus, the present or current OCP, i.e. the cathode potential in the zero-current state with respect to the reference system, is used as reference parameter for the potential of the cathode in the current-carrying state, i.e. during electrolysis operation. For this purpose, the voltage or current between the anode and cathode is adjusted by means of closed-loop control in such a way that the cathode potential with respect to the reference system has a given target progression. This defined progression has at least one phase at a cathodic level and at least one phase at an anodic level. The desired electrolysis proceeds during the cathodic phase, whereas the cathode is regenerated during the anodic phase. For the regeneration, it is sufficient when the potential of the cathode is briefly above the OCP.

In some embodiments, a galvanostatic operating regime is used that has a defined current progression with a sequence of phases with anodic and cathodic current level, with dynamic readjustment of the defined current progression with the measured OCP. In a first measurement, it is advisable to constantly determine the current OCP to which the current progression is to be aligned. In the case of fixed processes, it is more favorable under some circumstances to utilize a defined OCP progression.

In some embodiments, in the electrolysis method, a hydrocarbon is obtained from carbon monoxide or carbon dioxide in a single-stage process. With the above-defined specific pulsed voltage relative to the OCP, it is thus possible to produce the hydrocarbon with a high Faraday efficiency. Therefore, it is possible to save a correspondingly large amount of energy.

In some embodiments, a catalyst is used in the electrolysis method, especially one that contains copper. In the anodic phase, copper(I) oxide is formed at the cathode, which catalyzes the formation of $C_2H_x$. It is possible to use an aqueous electrolyte in the electrolysis method. This may be beneficial to the process and inexpensive to procure.

In some embodiments, the OCP changes during the analysis method. For example, the OCP can fall from a starting value to a system-related saturation value. In this case, the phase of the defined progression at an anodic level may also be correspondingly reduced, such that the reversal of polarity of the cathode can be somewhat smaller, as a result of which energy can be saved.

In some embodiments, the reference system used is a silver/silver chloride system or Ag/AgCl system. The silver electrode here in the silver chloride solution is the reference electrode, for example potentiostat. Such a reference system may be reliable, but it is also possible in principle to use other reference electrodes or reference systems.

In some embodiments, the working potential of the cathode in the current-carrying state and the OCP of the cathode in the zero-current state may be negative, with the working potential of the cathode simultaneously being temporarily at an anodic level. This means that the anodic level of the cathode can also be chosen at a negative level when the OCP is sufficiently negative. The anodic potential thus need not necessarily be positive, but may also be lower, as a result of which it is again possible to save energy.

In some embodiments, the working potential of the cathode at the anodic level may be below a starting OCP measurable at the start of the electrolysis method. As already indicated above, the OCP may fall from a starting OCP after a certain phase of operation to a saturation value. In this case, it is also favorable to likewise correspondingly lower the level of the anodic phase in order that the polarity reversal energy is reduced.

In periodic operation, there may be regular repetition of a duration of the phase at the anodic level of <10 s and a duration of the phase at the cathodic level of >10 s. Preferably, the duration of the phase at the anodic level is within a range from 2 s to 7 s, especially 5 s, and the duration of the phase at the cathodic level is within a range from 20 s to 100 s, especially within a range from 25 s to 50 s. With such a pulse structure and the abovementioned tracking of the anodic potential, it is possible to achieve a Faraday efficiency of more than 50% for the formation of $C_2H_4$, $CH_4$ and CO.

In some embodiments, any energy which is released on reversal of polarity of the cathode is stored in an intermediate storage means.

The intermediately stored energy can be utilized again in a subsequent cycle. This reuse can increase the efficiency of the electrolysis method.

In some embodiments, there is an electrolysis apparatus having an anode, a cathode, a reference system, and a voltage source for applying a pulsed voltage or a current source for establishing a pulsed current between the anode and the cathode, and having a measurement unit for repeated measurement of a respective current OCP that the cathode possesses in a zero-current state with respect to the reference system, and a control unit for controlling the pulsed voltage or the pulsed current between the anode and the cathode in such a way that a working potential of the cathode in the current-carrying state with respect to the reference system has a defined progression relative to the respective current OCP, wherein the defined progression has at least one phase at a cathodic level and at least one phase at an anodic level.

The possible variations and advantages described above in connection with the electrolysis method are applicable mutatis mutandis to the electrolysis device as functional features. The working examples outlined in detail hereinafter are example embodiments of the teachings herein. It should be noted here that the individual features can be implemented not just in the combination of features outlined but also on their own or in other technically viable combinations.

In some embodiments, rather than the customary steady-state operating point (potential/current density), for example in the electrochemical conversion of $CO_2$ or CO to hydrocarbons, a pulsed operating regime is employed. As shown in FIG. 1, the polarity of the working electrode which is negatively polarized in operation (cathode) is periodically reversed here to an anodic state relative to the OCP (open circuit potential) of the system. While the OCP is the potential of the cathode when there is no voltage between cathode and anode (zero-current state), the PF curve shows a pulse form or a target potential (defined progression) of the cathode during electrolysis operation (i.e. in the current-carrying state). This target potential has anodic phases $t_a$ above the OCP and cathodic phases $t_k$ below the OCP. The target voltage or the defined progression of the cathode voltage with respect to the reference system (e.g. Ag/AgCl) arises, for example, when a potentiostat is used to apply a correspondingly higher voltage between cathode and anode. The potentiostat controls a voltage between cathode and anode in such a way as to result in the target progression PF between the cathode and the reference electrode which is shown in FIG. 1.

In pulsed electrolysis, several aspects have to be considered. Firstly, a cleaning effect has to be expected at the electrode surface. However, this does not consist primarily in the removal of impurities but rather in the controlled corrosion of the catalyst surface (which has reduced activity after a period of time in constant operation) by formation of copper hydroxides/carbonates, or copper(I) oxide, and the subsequent reduction to copper, which is in turn deposited on the surface to form active high-index areas. In addition, copper(I) oxide formed also remains on the surface, which apparently catalyzes the formation of $C_2H_x$. It is essentially also possible in general to achieve continuous (re)formation of the catalyst. The catalyst material is consumed and is put back into operation by the reformation.

FIG. 1 shows a schematic pulse progression. It should be noted that the OCP is not necessarily constant. Instead, the OCP of a copper-containing cathode in an aqueous solution falls during electrolysis operation for example. However, the electrolysis apparatus is a carrier system, the OCP of which, according to the intensity of the preceding polarization, can need up to 1 hour in order to attain the original value again, if it is attained at all. As a result, there are two ways of configuring the pulses so as to minimize the energy losses mentioned at the outset:

a) By reducing the frequency of anodic pulses. The anodic pulses are required only for regeneration of the catalytic properties of the cathode.

b) The described inertia of the system allows attainment of an anodic effect with potentials below the initial OCP when the potential applied is anodic relative to the current OCP. This is the case, for example, when the OCP of initially −0.12 V versus Ag/AgCl drops to a present value of −0.20 V versus Ag/AgCl and the current anodic level is chosen as −0.18 V versus Ag/AgCl. In the present anodic operation, the potential of the cathode (−0.18 V) is below the initial OCP of −0.12 V but above the current OCP of −0.20 V.

One way of recovering energy is by the intermediate storage of the energy on reversal of polarity of the electrodes. When the regeneration process cycle is complete, there is no short-circuiting and destruction of the energy; instead, the voltage present at the electrodes after the end of the regeneration is discharged into an intermediate energy storage means and the charge is reused in the forthcoming cycle. A mere interruption of the cathodic operation, i.e. no anodic operation, by contrast, does not lead to any improvement in the process.

Figure 2:
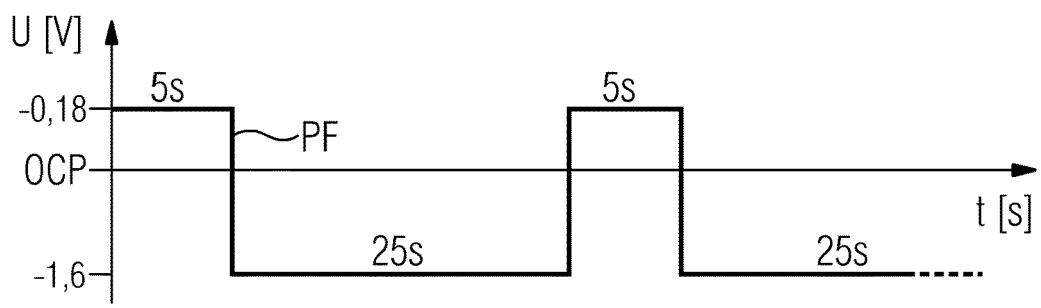
FIG. 2 an illustrative pulse profile with voltages versus Ag/AgCl.

In association with FIGS. 2 to 9, some examples are now presented, in which pulsed electrolysis is conducted with reference to the OCP potential. In one example, the pulse profile shown in FIG. 2 is used. The pulse profile shows the target progression of the voltage of the cathode during electrolysis operation (current-carrying state of the cathode)

relative to an Ag/AgCl reference system. This is a periodic pulse progression. A short anodic phase of 5 s is followed by a cathodic phase of 25 s. This is again followed by an anodic phase of 5 s etc. The potential in the anodic phase in the present example is −0.18 V and the potential in the cathodic phase is −1.6 V. The present OCP which is established after a certain operating time here is, for example, −0.20 V. It is thus well below the original OCP of −0.12 V. However, this also means that the anodic phase is below the original OCP but above the present OCP.

Figure 3:
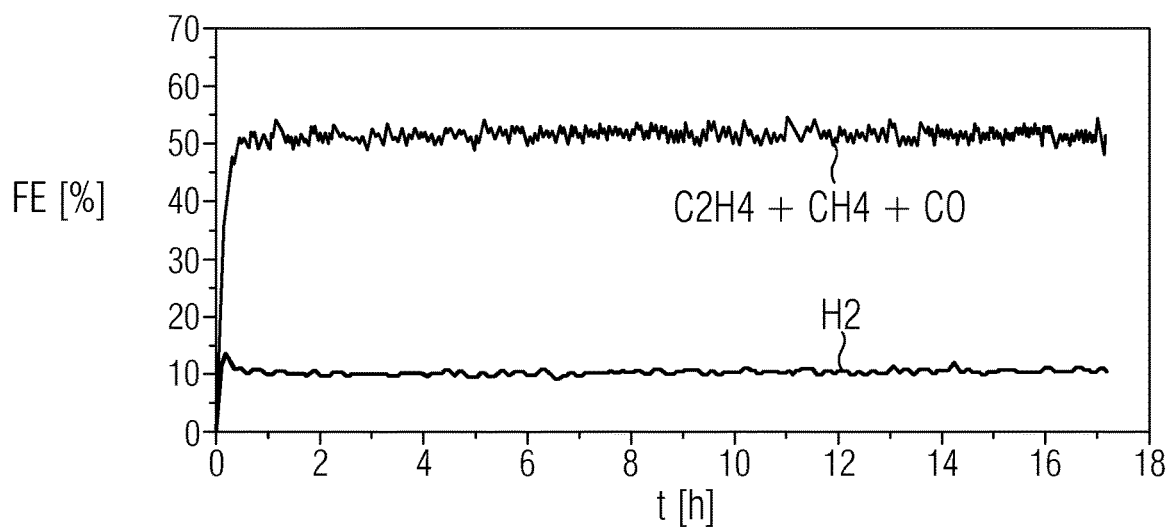
FIG. 3 the Faraday efficiency of gaseous products in the electrolysis of $CO_2$.
Figure 4:
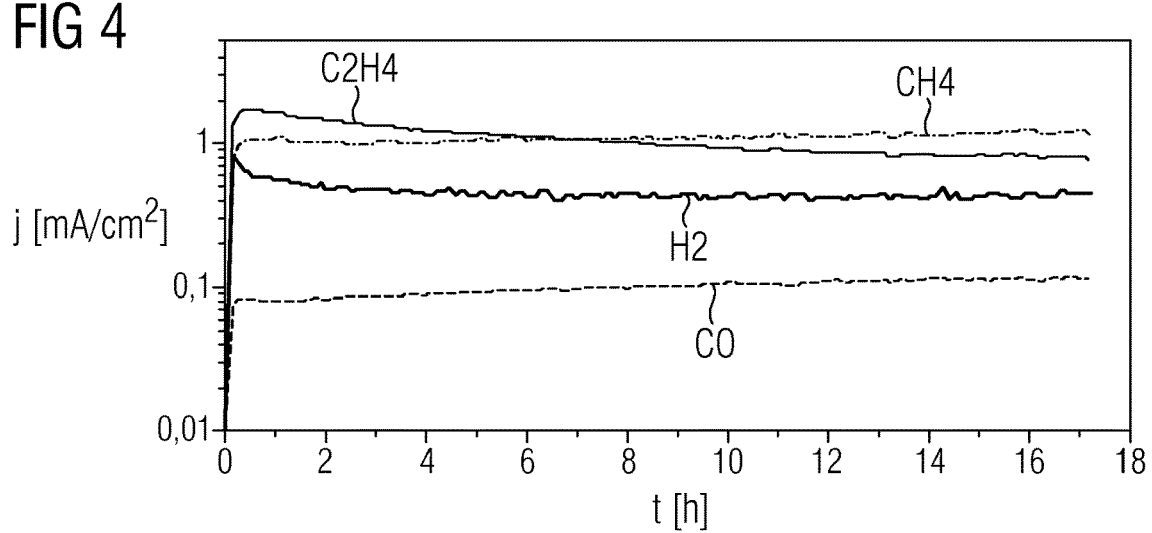
FIG. 4 partial current densities of the gaseous products.

With the mode of operation described, it is possible to suppress the evolution of $H_2$, which has to be regarded as a competing reaction to the processes desired. Given suitable choice of the pulse program (cf. FIG. 2), it was possible to form $H_2$ with just 10% Faraday efficiency over 17 hours, whereas $CH_4$, $C_2H_4$ and CO in total were formed with a constant efficiency of 50%, which is shown in FIG. 3. The evaluation of the current densities j shows, according to FIG. 4, a constant partial current density for $H_2$; that of CO and $CH_4$ rises slightly and the partial current density of $C_2H_4$ decreases a little.

Figure 5:
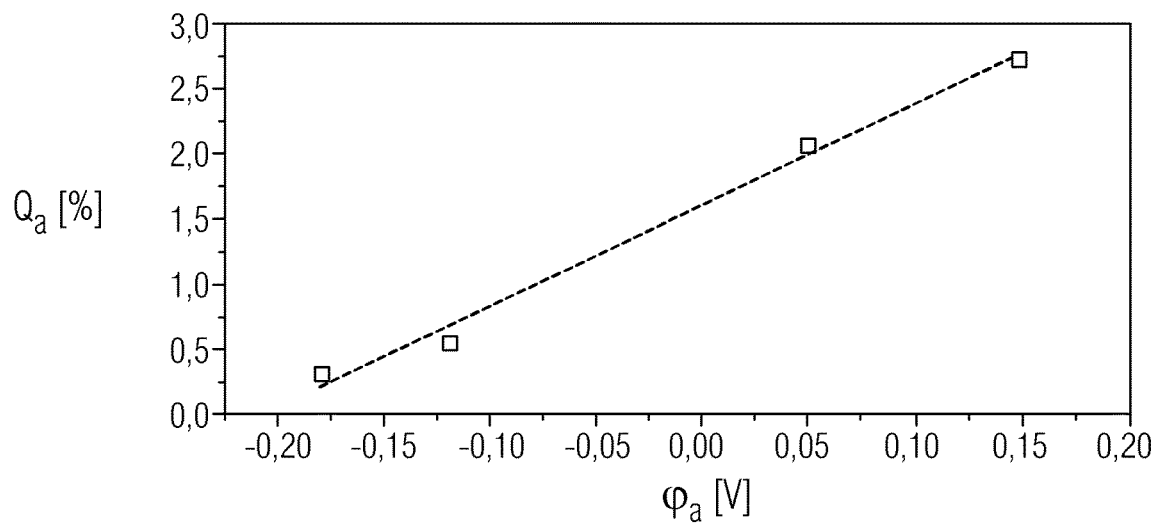
FIG. 5 a dependence of the anodic charge component on the anodic pulsed potential.

In association with FIG. 5, the effect of the level of the anodic potential on the consumption of energy is then illustrated. Anodic potentials $\varphi_a$ between −0.18 V and +0.15 V are examined. At an anodic potential of +0.15 V versus Ag/AgCl, the proportion $Q_a$ of the anodic charge, i.e. the charge which is consumed during the anodic pulse, is 2.7% of the total charge used per pulse cycle. At an anodic potential $\varphi_a$ of −0.18 V versus Ag/AgCl, it is just 0.3%.

Figure 6:
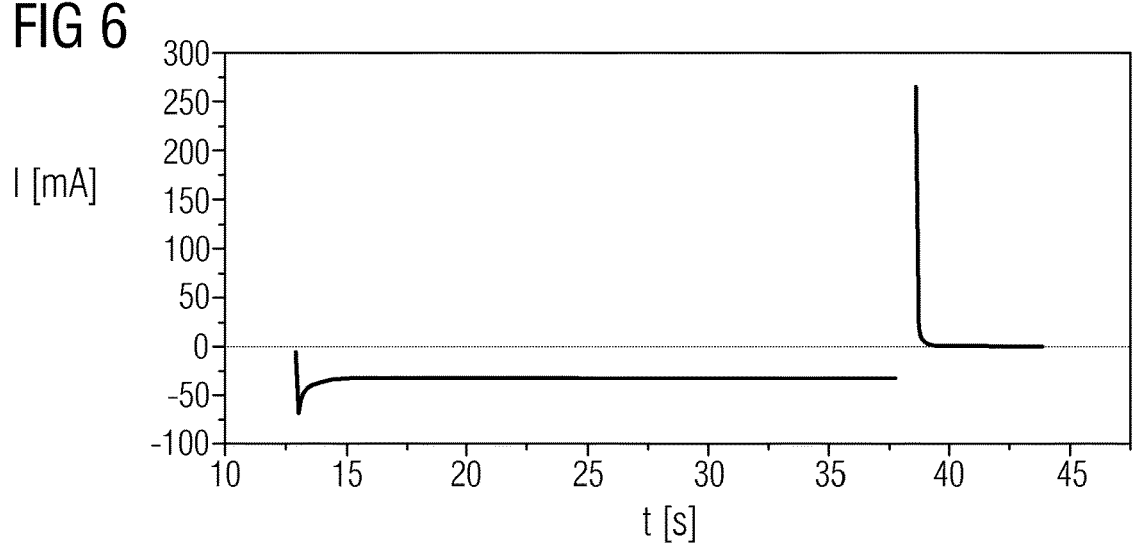
FIG. 6 a current response to a pulse cycle.

The representation of the current progression I against time t for a pulse cycle in FIG. 6 illustrates the charge ratio. An illustrative pulse cycle with −1.6 V over 25 s and +0.15 V over 5 s is used. During the cathodic 25 s, for instance, a current of −30 mA flows. During the anodic 5 s, by contrast, virtually no current flows. In the reversal of polarity from cathodic to anodic operation, however, a marked current spike is apparent, which results in a non-negligible consumption of energy. This consumption of energy can under some circumstances be attenuated by intermediate storage by means of a capacitor.

Figure 7:
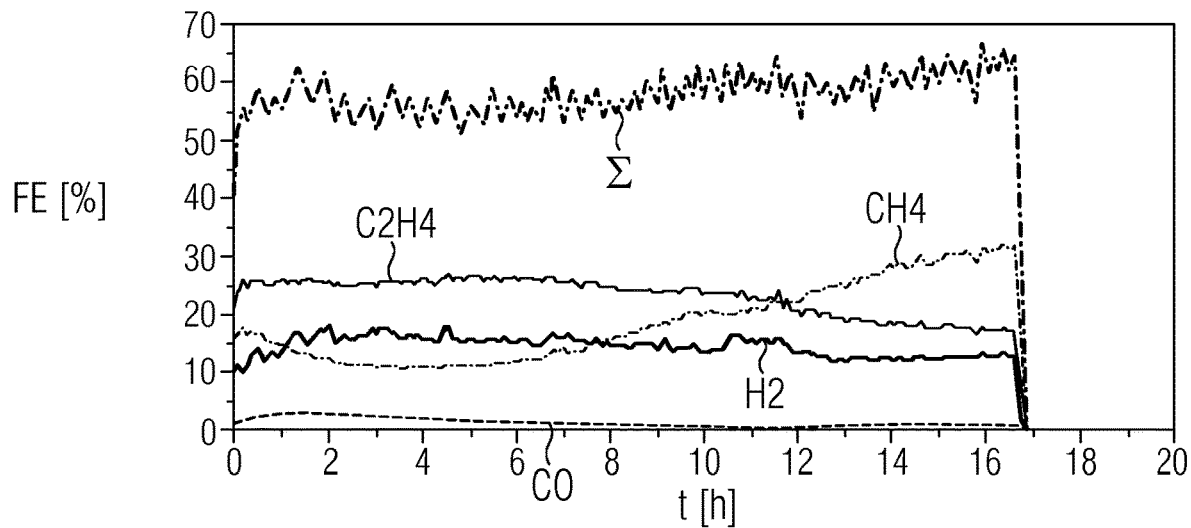
FIG. 7 a Faraday efficiency of gaseous products with a pulse program of 25 s, −1.6 V/5 s, +0.15 V.

With a pulse program that corresponds in form to that of FIG. 2 but pulses up to a potential of +0.15 V versus Ag/AgCl in the anodic components, it was possible to increase the selectivity for $C_2H_4$ over 8 hours versus conventional pulse forms. A corresponding result is shown in FIG. 7. In the first 10 hours, the Faraday efficiency for $C_2H_4$ is more than 25%. Subsequently, it drops somewhat and the selectivity for $CH_4$ rises. The sum total Σ of the Faraday efficiencies of all gaseous products CO, $H_2$, $CH_4$ and $C_2H_4$ is more than 50%.

Figure 8:
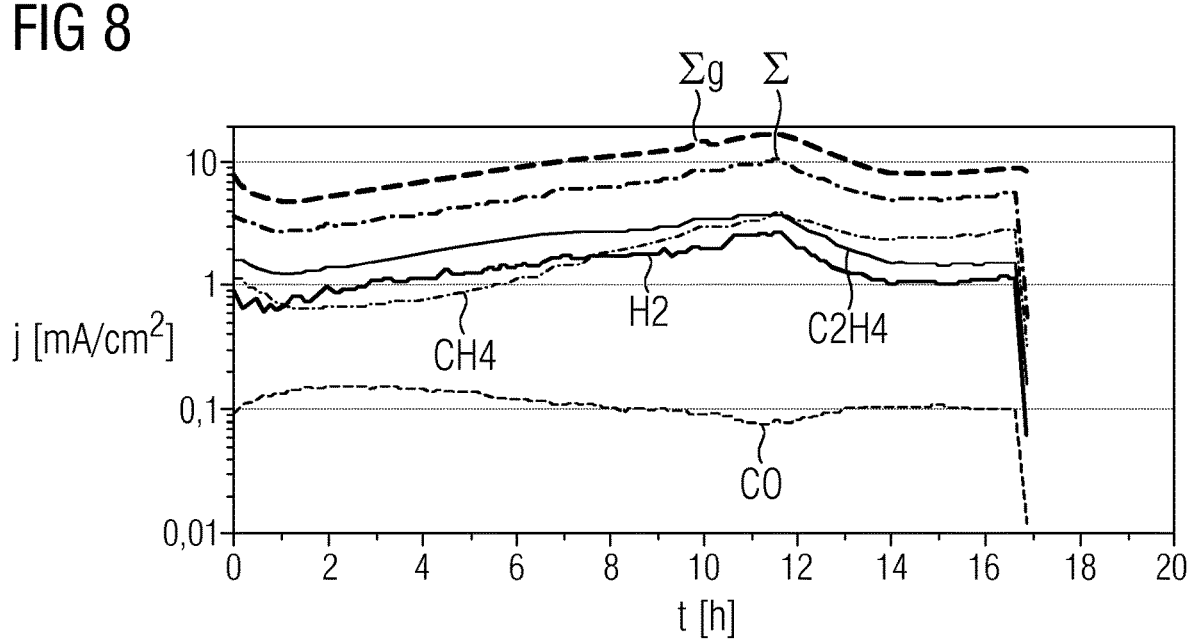
FIG. 8 partial current densities for the electrolysis of FIG. 7.

FIG. 8 shows the corresponding partial current densities j. Here too, the partial current density for $C_2H_4$ for a period of 10 hours is well above that of $CH_4$. As well as the sum total Σ for all gaseous products, the sum total $Σ_g$ for all products is shown, including the liquid products.

Figure 9:
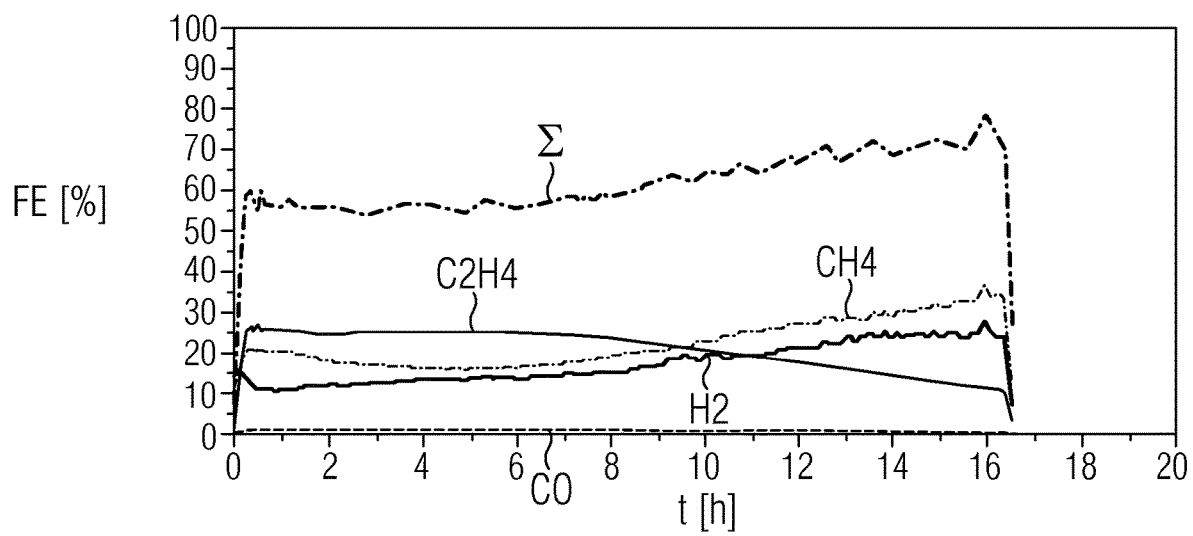
FIG. 9 the Faraday efficiency of gaseous products with a pulse program of 50 s, −1.6 V/5 s, +0.15 V.
Figure 10:
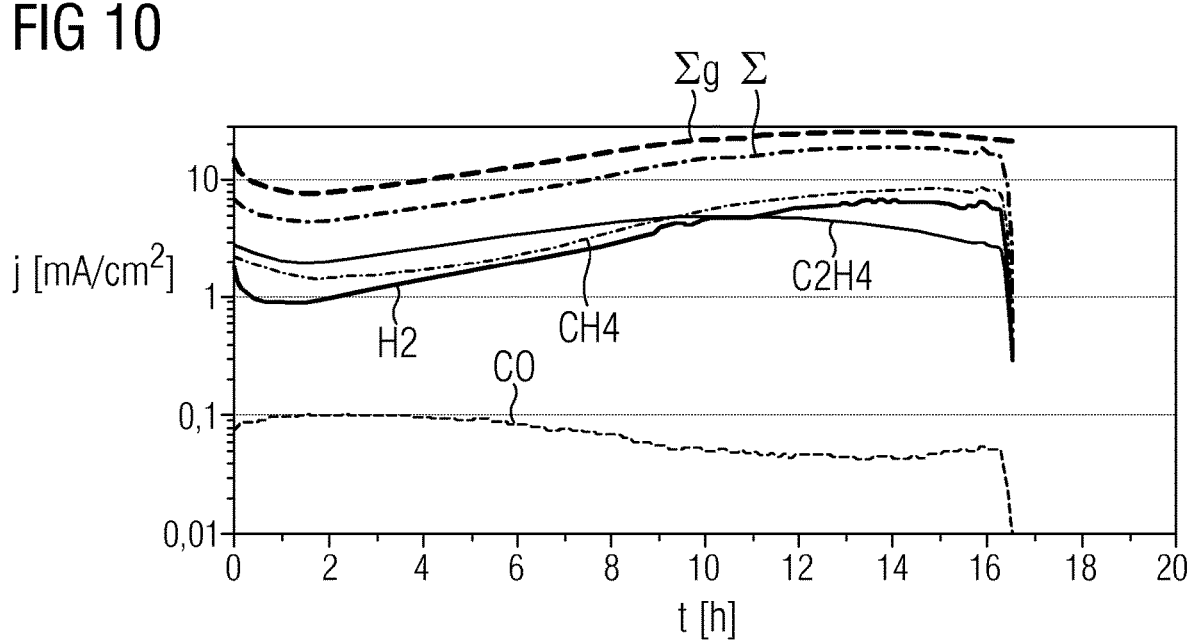
FIG. 10 partial current densities for the electrolysis of FIG. 9.

In addition, it is possible to reduce the number of anodic pulses without losing the positive effect on product formation. The pulse profile with the longest cathodic reaction time successfully verified to date consists of a cathodic phase (−1.6 V) with a duration of 50 s, followed by an anodic pulse (+0.15 V) of 5 s. The resulting Faraday efficiencies are shown in FIG. 9 and the resulting partial current densities in FIG. 10. Here too, it is apparent that the selectivity for $C_2H_4$ is above that of $CH_4$ for at least 8 hours. Specifically, the Faraday efficiency for $C_2H_4$ is roughly constant at 25% over 8 hours.

In summary, it can be stated that, in accordance with the present invention, pulsing takes place close to the current OCP, which avoids high losses in charge and energy. The OCP recovers only very slowly after cathodic polarization (e.g. −1.6 V), such that, even with potentials that are below the initial OCP but anodic relative to the current OCP, anodic polarization and hence a positive effect, for example on long-term stability, can be achieved.

The study of different pulse programs has additionally shown that it is not advisable to shorten the duration of the overall pulse cycle too significantly since, in the event of excessively high frequency, the proportion of capacitive currents and hence losses rises and the process can no longer be operated in an economically viable manner. It would thus likewise be advantageous to make the cathodic component in the configuration of the pulse sequence of relevance for product formation as long as possible and keep the anodic component required for the long-term stability and product selectivity as short as possible. For example, a pulse sequence of 50 s cathodic and 5 s anodic has a positive effect on long-term stability and product selectivity.

The avoiding of high losses by pulsing close to the OCP means that the use of this technique is also of interest for larger plants.

This would enable stable long-term electrolyses in aqueous electrolytes with permanent suppression of the evolution of $H_2$. Moreover, it is of possible at the same time to keep the selectivity/formation rate of products of value such as $C_2H_4$ and $CH_4$ essentially constant, with expenditure of very small proportions of energy.

What is claimed is:

1. An electrolysis method comprising:
   applying a pulsed voltage or a pulsed current between an anode and a cathode;
   repeatedly measuring a respective current OCP at the cathode in a zero-current state relative to a reference system;
   controlling the pulsed voltage or the pulsed current so a working potential of the cathode in the current-carrying state with respect to the reference system has a defined progression relative to the respective current OCP; and
   changing the OCP during performance of the electrolysis method;
   wherein the defined progression includes a first phase at a cathodic level and a second phase at an anodic level.

2. The electrolysis method as claimed in claim 1, further comprising using a galvanostatic operating regime having a defined current progression with a sequence of phases with anodic and cathodic current level;
   wherein the defined current progression is readjusted dynamically with the measured OCP.

3. The electrolysis method as claimed in claim 1, further comprising obtaining a hydrocarbon in a one-stage process from carbon monoxide or carbon dioxide.

4. The electrolysis method as claimed in claim 1, further comprising using a catalyst.

5. The electrolysis method as claimed in claim 1, further comprising using an aqueous electrolyte.

6. The electrolysis method as claimed in claim 1, wherein the reference system comprises a silver/silver chloride system.

7. The electrolysis method as claimed in claim 1, wherein the working potential of the cathode in the current-carrying state and the OCP are negative and, at the same time, the working potential of the cathode is temporarily at an anodic level.

8. The electrolysis method as claimed in claim 1, wherein the working potential of the cathode at the anodic level is below an initial OCP measurable at the start of the electrolysis method.

9. The electrolysis method as claimed in claim 1, further comprising regular repetition of a duration of the first phase below 10 s and a duration of the second phase above 10 s.

10. The electrolysis method as claimed in claim 9, wherein the duration of the first phase is within a range from 2 s to 7 s, and the duration of the second phase is within a range from 20 s to 100 s.

11. The electrolysis method as claimed in claim 1, wherein the pulsed voltage or the pulsed current has a square wave profile, a stepped profile, or a multilevel profile.

12. The electrolysis method as claimed in claim 1, further comprising storing any energy released on reversal of polarity of the cathode in an intermediate storage means.

13. An electrolysis apparatus comprising:
an anode;
a cathode;
a reference system;
a voltage source for applying a pulsed voltage or a current source for establishing a pulsed current between the anode and the cathode;
a measurement unit for repeated measurement of a respective current OCP at the cathode in a zero-current state with respect to the reference system; and
a control unit for controlling the pulsed voltage or the pulsed current so a working potential of the cathode in the current-carrying state with respect to the reference system has a defined progression relative to the respective current OCP;
wherein the defined progression includes a first phase at a cathodic level and a second phase at an anodic level; and
the control unit changes the OCP during electrolysis.

14. An electrolysis method comprising:
applying a pulsed voltage or a pulsed current between an anode and a cathode;
repeatedly measuring a respective current OCP at the cathode in a zero-current state relative to a reference system; and
controlling the pulsed voltage or the pulsed current so a working potential of the cathode in the current-carrying state with respect to the reference system has a defined progression relative to the respective current OCP;
wherein the defined progression includes a first phase at a cathodic level and a second phase at an anodic level; and
the working potential of the cathode at the anodic level is below an initial OCP measurable at the start of the electrolysis method.

15. The electrolysis method as claimed in claim 14, further comprising using a galvanostatic operating regime having a defined current progression with a sequence of phases with anodic and cathodic current level;
wherein the defined current progression is readjusted dynamically with the measured OCP.

16. The electrolysis method as claimed in claim 14, further comprising obtaining a hydrocarbon in a one-stage process from carbon monoxide or carbon dioxide.

17. The electrolysis method as claimed in claim 1, wherein the reference system comprises a silver/silver chloride system.

18. The electrolysis method as claimed in claim 1, wherein the working potential of the cathode in the current-carrying state and the OCP are negative and, at the same time, the working potential of the cathode is temporarily at an anodic level.

19. The electrolysis method as claimed in claim 14, further comprising regular repetition of a duration of the first phase below 10 s and a duration of the second phase above 10 s.

20. The electrolysis method as claimed in claim 19, wherein the duration of the first phase is within a range from 2 s to 7 s, and the duration of the second phase is within a range from 20 s to 100 s.

21. An electrolysis apparatus comprising:
an anode;
a cathode;
a reference system;
a voltage source for applying a pulsed voltage or a current source for establishing a pulsed current between the anode and the cathode;
a measurement unit for repeated measurement of a respective current OCP at the cathode in a zero-current state with respect to the reference system; and
a control unit for controlling the pulsed voltage or the pulsed current so a working potential of the cathode in the current-carrying state with respect to the reference system has a defined progression relative to the respective current OCP;
wherein the defined progression includes a first phase at a cathodic level and a second phase at an anodic level; and
the control unit changes the OCP during electrolysis.

* * * * *